United States Patent [19]

Okazaki

[11] Patent Number: 5,062,412
[45] Date of Patent: Nov. 5, 1991

[54] SHOCK WAVE GENERATING APPARATUS FORMING WIDE CONCRETION-DISINTEGRATING REGION BY FOCUSED SHOCK WAVE

[75] Inventor: Kiyoshi Okazaki, Tochigi, Japan

[73] Assignee: Kabushiki Kaisha Toshiba, Kawasaki, Japan

[21] Appl. No.: 426,546

[22] Filed: Oct. 26, 1989

[30] Foreign Application Priority Data

Oct. 31, 1988 [JP] Japan .................. 63-276628

[51] Int. Cl.$^5$ ............................................. A61B 17/22
[52] U.S. Cl. ............................ 128/24 OEL; 128/804
[58] Field of Search ............ 128/24 AA, 24 EL, 804, 128/660.03; 367/138; 181/142

[56] References Cited

U.S. PATENT DOCUMENTS

| | | | |
|---|---|---|---|
| 4,526,168 | 7/1985 | Hassler et al. | 128/24 FL |
| 4,617,931 | 10/1986 | Dory | 128/328 |
| 4,622,972 | 11/1986 | Giebeler, Jr. | 128/24 AA |
| 4,646,756 | 3/1987 | Watmough et al. | 128/804 |
| 4,757,820 | 7/1988 | Itoh | 128/24 AA |

FOREIGN PATENT DOCUMENTS

| | | |
|---|---|---|
| 3736733 | 5/1988 | Fed. Rep. of Germany . |
| 2567394 | 1/1986 | France . |
| 2287893 | 4/1987 | France . |

Primary Examiner—Ruth S. Smith
Attorney, Agent, or Firm—Finnegan, Henderson, Farabow, Garrett, and Dunner

[57] ABSTRACT

To electrically and simultaneously form a plurality of focused regions of shock waves, a shock wave generating apparatus comprises: a plurality of high-voltage pulse generators for generating a plurality of high-voltage pulses; a shock wave generating unit having a plurality of ultrasonic vibrating element groups, coupled to the plurality of high voltage pulse generators, for generating shock waves and for focusing the shock waves onto a plurality of different focused regions within a biological body under examination; and a plurality of delay units coupled via the high-voltage pulse generators to the plural ultrasonic vibrating element groups, for causing the plurality of high-voltage pulses having predetermined delay times to be generated from the high-voltage pulse generators, whereby the plural focused regions are simultaneously formed juxtaposed each other near a concretion to be disintegrated with the biological body.

6 Claims, 12 Drawing Sheets

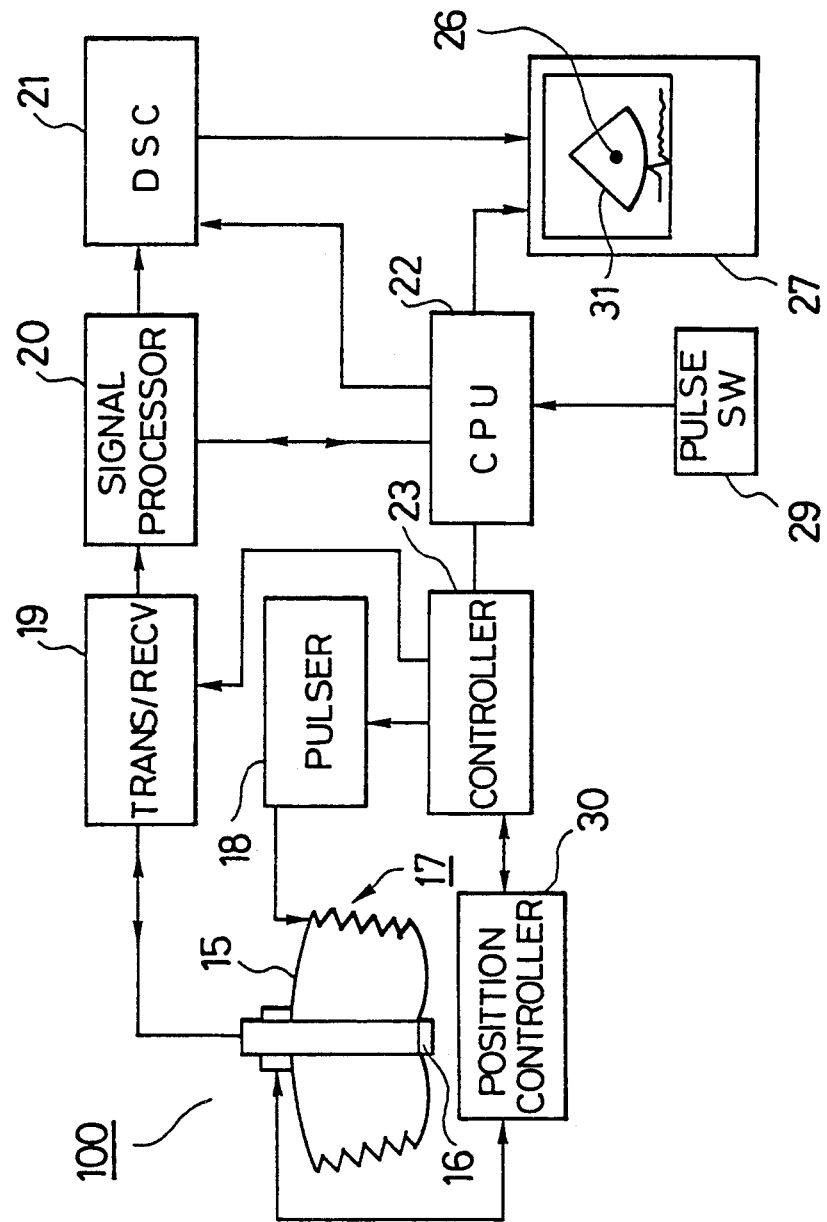

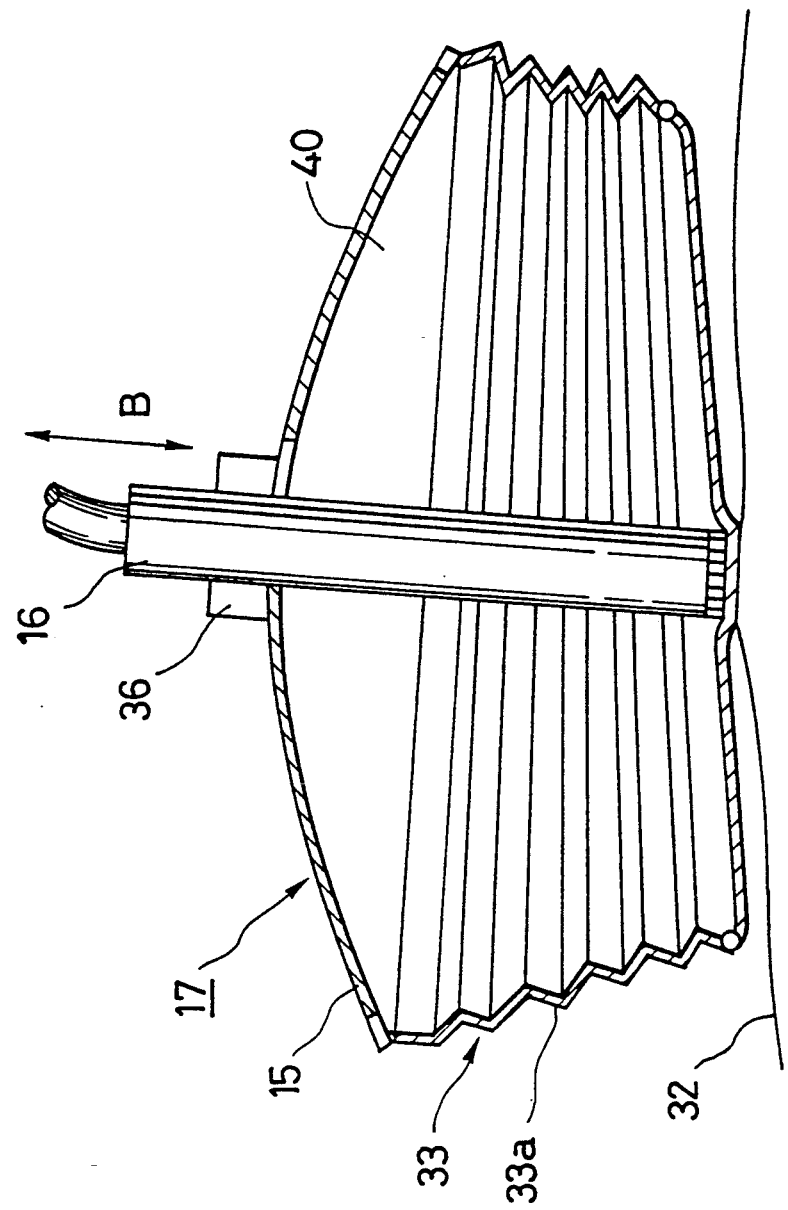

5,062,412

SHOCK WAVE GENERATING APPARATUS FORMING WIDE CONCRETION-DISINTEGRATING REGION BY FOCUSED SHOCK WAVE

BACKGROUND OF THE INVENTION

1. Field of the Invention

The present invention generally relates to a shock wave generating apparatus capable of disintegrating an object within a biological object under medical examination, e.g., a cancer cell, and a concretion by utilizing focused energy of shock waves. More specifically, the present invention is directed to a shock wave generating apparatus capable of generating a wide concretion-disintegrating region by the focused shock waves.

2. Description of the Related Art

Various types of shock wave generating apparatuses have been proposed in, for instance, Japanese KOKAI (Disclosure) patent application No. 62-49843 (1987). In FIG. 1, there is shown, as a sectional view, an ultrasonic wave applicator of one conventional shock wave generating apparatus.

The construction of this ultrasonic wave application is as follows. A through hole having a predetermined shape is formed in a center portion of this applicator 1. A vibrating element (e.g., piezoelectric transducer element) 2 is spherically formed and a backing material 3 is uniformly adhered to a rear surface of this spherical vibrating element 2. An imaging ultrasonic probe 4 is positioned in such a manner that a transmitting/receiving wave front (ultrasonic array) 4a is located at the curved surface identical to the shock wave transmitting/receiving wave front of the vibrating element 2, or backward the last-mentioned wave front. Furthermore, this ultrasonic wave applicator 1 includes a water bag 5 containing water as a coupling medium for the ultrasonic wave. Reference numeral 6 indicates a biological body under medical examination.

To disintegrate a concretion or calculus within a biological body by utilizing the above-described conventional shock wave generating apparatus, the focal point of the generated shock wave must be pointed to this concretion, which will be referred to as "a positioning of a focal point". Such a positioning of a focal point is performed under the condition that while both a B-mode image (tomographic image) of the biological body and a marker indicative of the focal point are displayed on the display means, this focal point marker is tried to be coincident with the concretion displayed on the display screen. This conventional focal point positioning is described in, for instance, U.S. Pat. No. 4,617,931 to J. Dory entitled "ULTRASONIC PULSE APPARATUS FOR DESTROYING CALCULUSES" issued on Oct. 21, 1986. It should be noted that the marker indicates the focal point defined by the geometrical parameters of the vibrating element 2.

FIGS. 2A to 2C illustrate relationships between the shock wave front and focused region in the conventional shock wave generating apparatus shown in FIG. 1.

In FIG. 2A, reference numeral 7 indicates a single focused region of the shock wave transmitted from the vibrating element 2. This vibrating element 2 is subdivided into six portions as illustrated in FIG. 2B, and the six portions are arranged in a spherical form as represented in FIG. 2A. It should be noted that only one focused region 7 is formed from six element portions "a" to "f". FIG. 2C is an illustration of the focused region 7 as viewed from the transmission direction of the shock wave toward an object 8 to be disintegrated.

Assuming now that an area indicative of a half value of a peak pressure produced by a shock wave transmitted from a vibrating element is defined as the above-described focused region 7, this focused region 7 is geometrically determined by the diameter of the spherical body and the aperture of the vibrating element 2. As apparent from FIG. 2C, since a size of this focused region 7 is very small as compared with the object 8 to be disintegrated within the biological body, the calculus disintegrating efficiency by the shock wave is considerably lowered, which necessarily requires a large quantity of time so as to completely disintegrate the object 8.

The present invention has been made in an attempt to solve the above-described problems of the conventional shock wave generating apparatus, and therefore, has an object to provide a shock wave generating apparatus capable of improving the concretion disintegrating efficiency with respect to the object to be disintegrated within the biological body.

SUMMARY OF THE INVENTION

The above-described object and other features of the present invention are accomplished by providing a shock wave generating apparatus (100) comprising:

high-voltage pulse generating means (18) for generating a high-voltage pulse; and, shock wave generating means (15:25) having a plurality of ultrasonic vibrating element groups (10a: 10g), coupled to the high-voltage pulse generating means (18), for generating shock waves and for focusing the shock waves onto a plurality of different focused regions (11a: 11g) within a biological body (32) under examination by selecting a geometrical parameter of the respective ultrasonic vibrating element groups (10a: 10g), whereby the plural focused regions (11a: 11g) are simultaneously formed juxtaposed each other near an object (8) to be disintegrated within the biological body (32).

Furthermore, a shock wave generating apparatus (200) according to the invention is characterized by comprising:

a plurality of high-voltage pulse generating means (18-1: 18-7) for generating a plurality of high-voltage pulses;

shock wave generating means (15: 25) having a plurality of ultrasonic vibrating element groups (10a: 10g), coupled to said plurality of high-voltage pulse generating means (18-1: 18-7), for generating shock waves and for focusing the shock waves onto a plurality of different focused regions (11a: 11g) within a biological body (32) under examination; and, a plurality of delay means (50: 51) coupled via said plurality of high-voltage pulse generating means (18-1: 18-7) to said plurality of ultrasonic vibrating element groups (10a: 10g), for causing a plurality of high-voltage pulses having predetermined delay times to be generated from the high-voltage pulse generating means (18-1: 18-7), whereby the plural focused regions (11a: 11g) are simultaneously formed juxtaposed each other near an object (8) to be disintegrated within the biological body (32).

In addition, a shock wave generating apparatus (300) according to the invention is characterized by comprising:

a plurality of high-voltage pulse generating means (18-1: 18-7) for generating a plurality of high-voltage pulses;

shock wave generating means (15: 25) having a plurality of ultrasonic vibrating element groups (10a: 10g), coupled to said plurality of high-voltage pulse generating means (18-1: 18-7), for generating shock waves onto a plurality of different focused regions (11a: 11g) within a biological body (32) under examination;

a plurality of delay means (50: 51) coupled via said plurality of high-voltage pulse generating means (18-1: 18-7) to said plurality of ultrasonic vibrating element groups (10a: 10g), for causing a plurality of high-voltage pulses having predetermined delay times to be successively generated from the high-voltage pulse generating means (18-1: 18-7); and, multiplexing means (55) interposed between said plurality of high-voltage pulse generating means (18-1: 18-7) and said plurality of ultrasonic vibrating element groups (10a: 10g), for multiplexing said plurality of high-voltage pulses having the predetermined delay times, whereby the plural focused regions (11a: 11g) are successively formed juxtaposed each other near an object (8) to be disintegrated within the biological body (32).

Accordingly, since a plurality of focused regions by the shock waves are simultaneously, or time-sequentially formed near or at the calculus, the calculus can be quickly disintegrated.

BRIEF DESCRIPTION OF THE DRAWINGS

For a better understanding of the present invention, reference is made to the following description in conjunction with the accompanying drawings, in which:

FIG. 3 is a schematic block diagram of a shock wave generating apparatus 100 according to a first preferred embodiment of the invention;

FIG. 5 is a cross-sectional view of the shock wave applicator, taken along a line A—A represented in FIG. 4;

DETAILED DESCRIPTION OF THE PREFERRED EMBODIMENTS

Basic Idea

Figure 1:
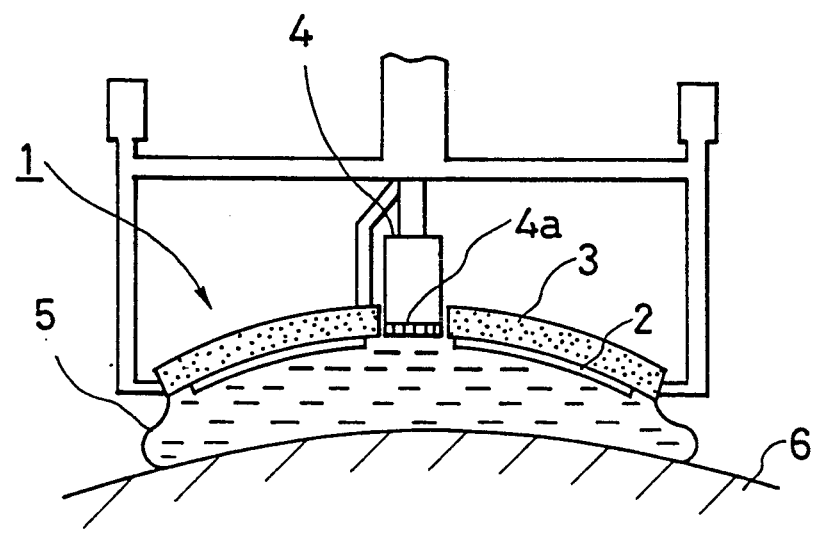
FIG. 1 is a sectional view of an ultrasonic pulse applicator employed in a conventional shock wave generating apparatus.

The major feature of the present invention is achieved as follows. To enlarge an area of an effective focused region of shock waves transmitted from vibrating elements toward an object to be disintegrated (i.e., a region indicative of a half peak value of the shock wave pressure in a direction perpendicular to the transmission direction of the shock wave), the vibrating elements are driven by the following three typical methods.

1) A geometrical parameter (shape, relative position, etc.) of the respective vibrating elements constituting each of the vibrating element groups, is properly selected in such a manner that the plural focused regions formed by the respective vibrating element groups are simultaneously formed juxtaposed each other;

2) A shock wave generating means is formed by employing a plurality of vibrating element groups each having plural vibrating elements. Plural focused regions defined by the shock waves transmitted from the respective vibrating elements in the corresponding vibrating element groups are simultaneously formed under the condition that these focused regions are juxtaposed each other. Such a condition is achieved by, for instance, driving the respective vibrating elements with a predetermined delay time.

3) An element driving timing is electronically controlled in such a manner that one of the plural focused regions defined by the respective vibrating element groups is successively formed. In other words, a relatively small single focused region defined by each of the vibrating element groups is scanned over a large object to be disintegrated.

In accordance with the present invention, as previously described, the shock wave generating means is constructed of a plurality of vibrating element groups from which a plurality of shock waves are geometrically focused onto a plurality of focused regions, and these plural focused regions are juxtaposed each other by taking account of the positional relationship geometrical parameter among the vibrating elements. Accordingly, a synthesized size or area of these focused regions is relatively larger than the size of the single focused region of the conventional shock wave generating apparatus, so that the disintegrating efficiency of the object (e.g. calculus) to be disintegrated can be considerably improved. In this case, each of the focused regions by the respective vibrating element groups is geometrically defined. In other words, the forming positions of the focused regions are determined by controlling the geometrical parameters (dimension, shape) of the vibrating element groups. Moreover, according to the present invention, such a formation of the plural focused regions can be electronically realized. That is, the driving timings of the respective vibrating elements are controlled by the driving timing control means in such a manner that the respective focused regions are formed with being juxtaposed with each other. Similarly, the disintegrating efficiency achieved by this electronic element driving control can be improved, as same as in the above-described geometrical element control. Alternatively, the formation timings of these focused regions may be time-sequentially shifted.

Circuit Arrangement of First Shock Wave Generator

A shock wave generating apparatus 100 according to a first preferred embodiment of the invention will now be described, which is accomplished based upon the above-described first basic idea.

FIG. 3 is a schematic block diagram of the first shock wave generating apparatus 100. The first shock wave generating apparatus 100 includes an ultrasonic pulse applicator 17 containing a shock wave generating means 15 for generating the shock wave, and an ultrasonic imaging probe 16 for transmitting/receiving the ultrasonic pulses. This shock wave generating apparatus 100 further includes a pulser 18 for supplying a high-voltage driving pulse to the shock wave generating means 15; a transmitter/receiver circuit 19 for transmitting a low-voltage pulse to the ultrasonic imaging probe 16 and also for receiving an echo signal derived from the ultrasonic imaging probe 16; and a signal processor 20 for fetching the output signal derived from the transmitter/receiver circuit 19 so as to amplitude-detect this output signal to obtain a video signal. The shock wave generating apparatus 100 also includes a central processing unit (referred to as a "CPU") for controlling various operations of the circuitry employed in this apparatus 100; a controller 23 for controlling the transmitting/receiving timings, amplitudes and frequencies of the pulse signals for the transmitter/receiver circuit 19, signal processing circuit 20, and pulser 18 under the control of CPU 22, a digital scan converter 21 for performing a signal process on the output signal derived from the signal processor 20; a display unit 27 for displaying a B-mode (tomographic) image 25, a focal point maker 26 and the like thereon, based upon the signal output from the digital signal converter 21; a pulse generating switch 29 connected to CPU 22, for setting a generation timing of the high-voltage driving pulse signal transmitted from the pulser 18 to the shock wave generating means 15; and also a position control 30 for adjusting a relative positional relationship between the shock wave generating means 15 and the ultrasonic imaging probe 16.

Construction of Shock Wave Applicator

A construction of the shock wave applicator 17 will now be described in detail.

Figure 4:
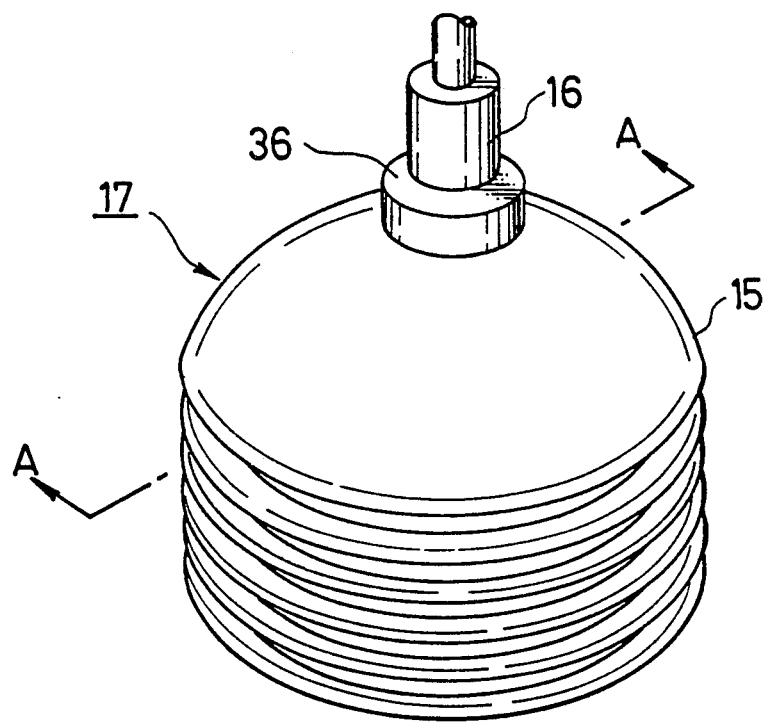
FIG. 4 is a perspective view of a shock wave applicator employed in the first shock wave generating apparatus 100 shown in FIG. 13.

FIG. 4 is a perspective view of the shock wave applicator 17, and FIG. 5 is a cross-sectional view of the shock wave applicator 17, taken along the line A—A of FIG. 4.

As shown in FIG. 5, the ultrasonic imaging probe 16 is moved along an arrow "B" by a probe supporting/driving unit 36. A water bag 33 is provided and has a bellows unit 33a for flexibility purposes. Water 40 is injected into the water bag 33 so as to transfer the generated shock wave inside the biological body 32 at a higher efficiency.

Geometrical Arrangement of Vibrating Elements

Figure 6A:
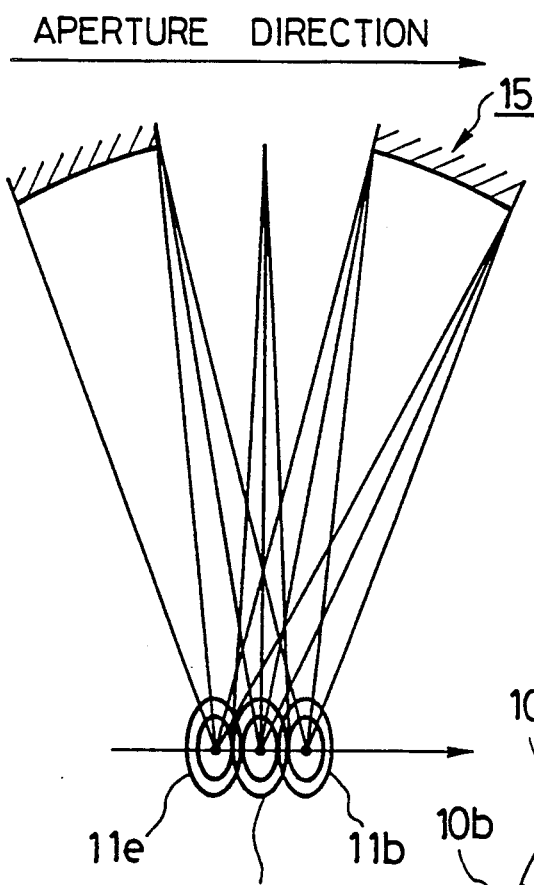
FIGS. 6A to 6D are illustrations for schematically explaining the formation of the plural focused regions of the shock waves by the shock wave applicator shown in FIG. 4.
Figure 6B:
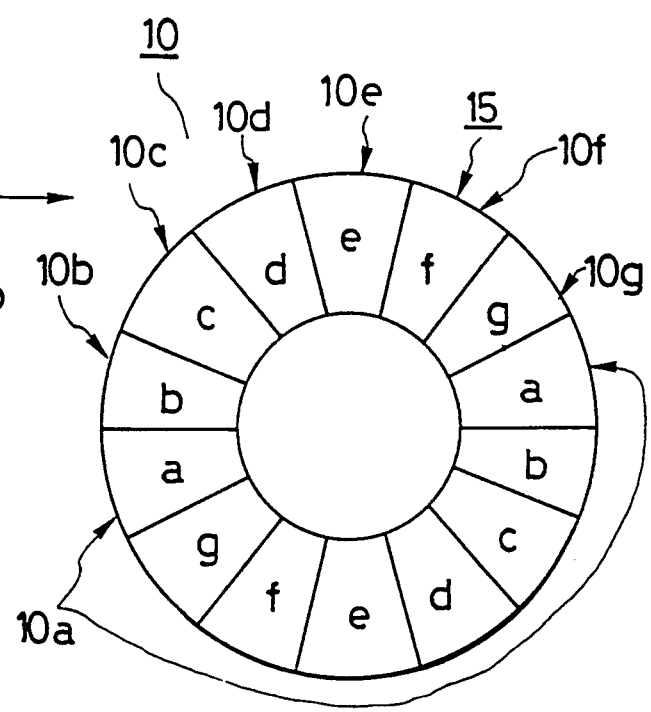
Figure 6C:
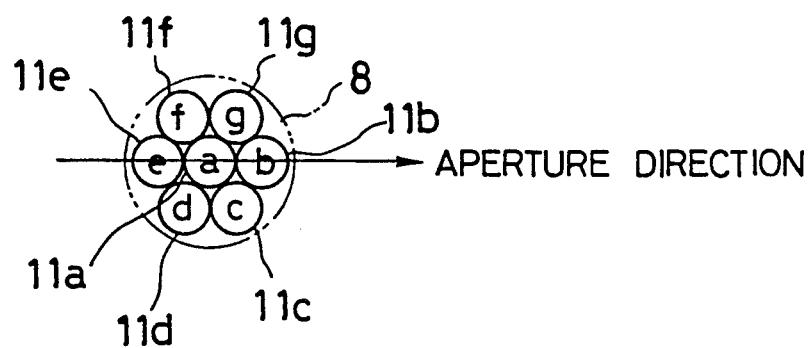

Referring now to FIGS. 6A to 6C, the shock wave generating means 15 will be described in detail. FIGS. 6A to 6C pictorially represent the relationships between the shock wave front and the focused regions in the shock wave generating apparatus 100. As illustrated in FIGS. 6A and 6B, this shock wave generating means 15 is constructed in such a manner that a plurality of ultrasonic vibrating elements, e.g., 14 pieces of the piezoelectric transducer elements are arranged in an endless form, and the wave front of the generated shock wave is a substantially spherical shape. The shock wave generating means 15 includes a plurality of vibrating element groups, e.g., 7 groups from which the geometrically focused shock waves are produced. That is to say, a first vibrating element group 10a is formed by one pair of vibrating elements denoted by "a" in FIG. 6B; a second vibrating element group 10b is formed by a pair of vibrating elements indicated by "b" in FIG. 6B; a sixth vibrating element group 10f is constructed of a pair of vibrating elements denoted by "f" shown in FIG. 6B; and furthermore a seventh vibrating element 10g group is formed by one pair of vibrating elements denoted by "g" shown in FIG. 6B. As illustrated in FIG. 6B, one pair of vibrating elements "a" to "g" constituting the respective vibrating element groups 10a to 10g are positioned on diagonal lines. It should be noted that for the sake of the simplicity, arrows for denoting the respective vibrating element groups 10b to 10g are attached only to one vibrating element constructing the respective element groups.

As these vibrating elements for producing the shock waves, for instance, a piezoelectric transducer element may be employed. A high-voltage drive pulse voltage from about 1 to 3 KV is applied to the vibrating elements which will be vibrated at a high frequency of, e.g., 500 KHz. Under these vibrating conditions, high pressure of approximately 1,000 bars is produced at the focused region, by which a desired shocking pressure can be obtained.

To apply such a high drive pulse voltage, the vibrating element groups 10 are connected to the pulser 18 represented in FIG. 3.

It should be noted that a relatively lower drive pulse voltage of, e.g., 100 V than the above-described drive pulse voltage is applied to the imaging probe 16 so as to obtain the B-mode tomographic image.

FIG. 6C illustrates the respective focused regions which are simultaneously formed by driving the vibrating element groups 10a to 10g, as viewed in the shock wave transmission direction. It should be noted that although the shapes of these focused regions are circle, the actual shapes thereof are elliptic or oval.

Figure 2A:
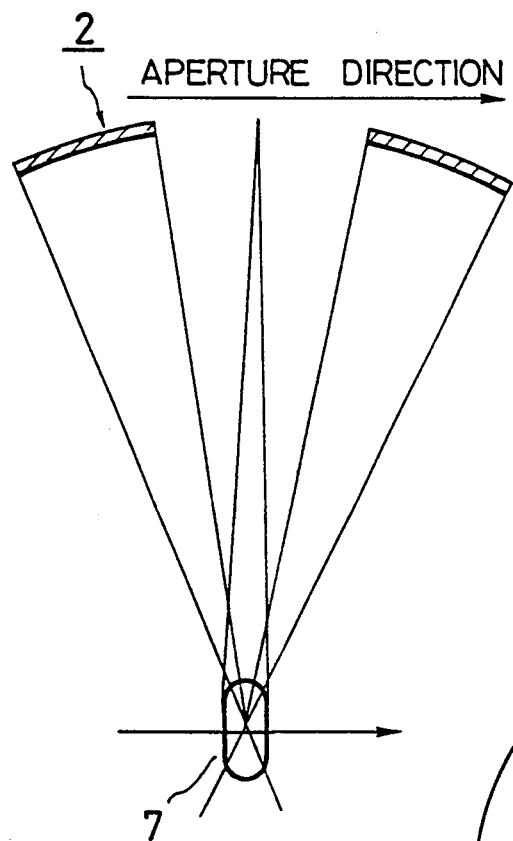
FIGS. 2A to 2C are illustrations for schematically explaining the formation of the single focused region of the shock waves produced by the ultrasonic pulse applicator shown in FIG. 1.
Figure 2B:
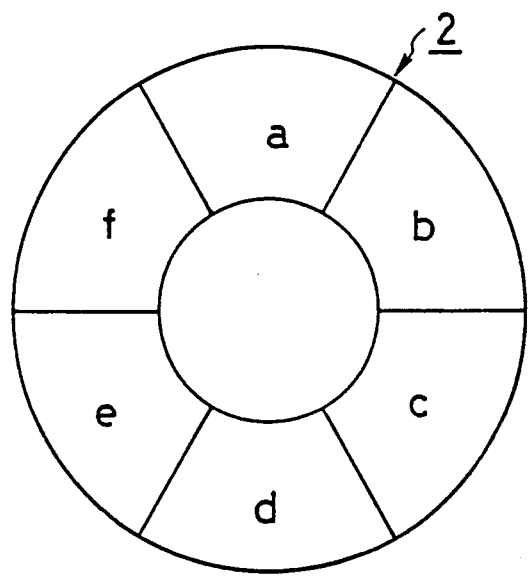
Figure 2C:
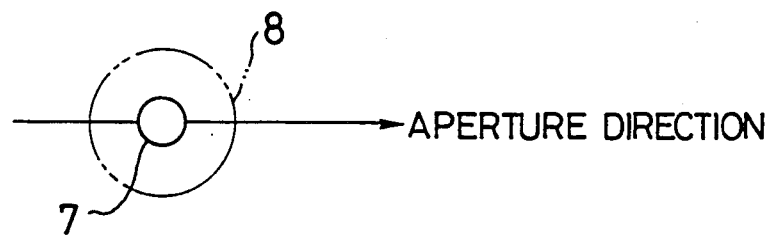

As previously described, one pair of vibrating elements "a" and "a" constituting the first vibrating element group 10a are positioned in such a manner that the shock waves transmitted from these vibrating elements "a" and "a" are synthesized at a first position geometrically defined so as to form a first focused region 11a. Another pair of vibrating elements "b" and "b" constituting the second vibrating element group 10b are positioned in such a manner that the shock waves transmitted from these vibrating elements "b" and "b" are synthesized at a second position geometrically defined, thereby forming a second focused region 11b. Similarly, the respective vibrating elements for constituting the third, fourth, fifth, sixth and seventh vibrating element groups 10c, 10d, 10e, 10f, and 10g are so arranged as to form third to seventh focused regions 11c to 11g, respectively, at geometrically defined areas. These focused regions 11a to 11g are formed at the same time under the condition that the simultaneously formed focused regions are juxtaposed with each other, as illustrated in FIG. 6C. As a consequence, a synthesized effective focused region by the first through seventh focused regions 11a to 11g is about 7 times larger than each of these focused regions 11a to 11g. In other words, since the resultant effective focused region simultaneously formed with juxtaposing a plurality of focused regions 11a to 11g with each other according to the first preferred embodiment can be made considerably larger than the single focal point 7 (see FIG. 2C) formed in the conventional shock wave generating apparatus, the effective disintegrating efficiency for the object to be disintegrated can be improved according to the invention.

Design of Focused Region

Figure 6D:
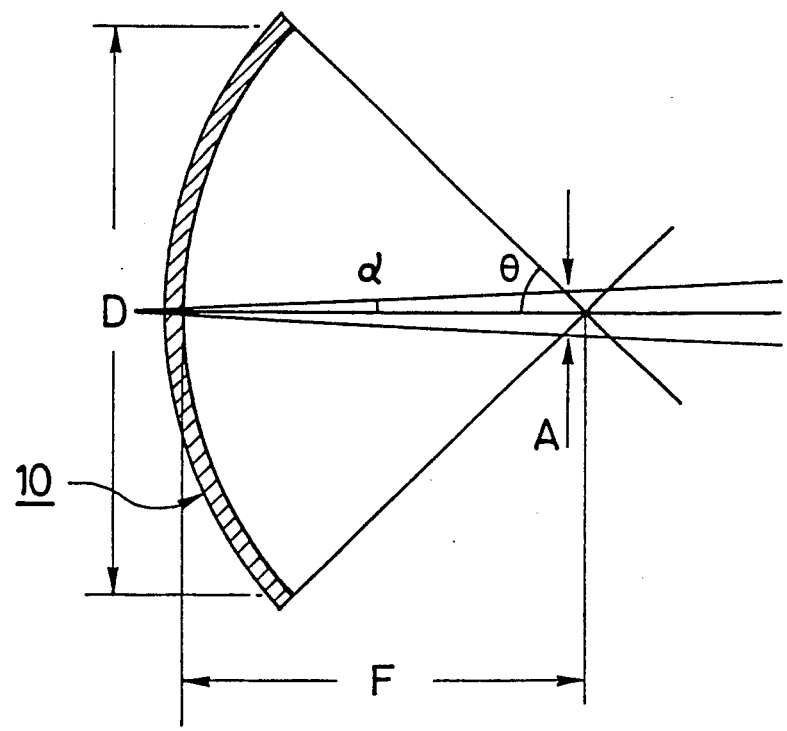

Then, the size of the respective focused regions geometrically defined by the shock waves is designed based upon the following approximate expression, according to the present invention, with reference to FIG. 6D.

For a better understanding of a drawing, it is assumed in FIG. 6D that a vibrating element group body 10 constructed of the seven vibrating element groups 10a to 10g is arranged in a parabolic form. An aperture of this vibrating element group body 10 is defined as "D", a geometrical focal distance defined by the vibrating element group body 10 is "F", and furthermore a size of a focused region (namely, a region representative of a half peak value of a shock wave) in the aperture direction is "A". Then, the following approximate equation is obtained:

$$\alpha = \sin^{-1}\left(1.22 \frac{C}{D \cdot f}\right) \quad (1)$$

where "$\alpha$" denotes an angle with respect to a center line of the vibrating element group body 10, "C" indicates an acoustic velocity, e.g., 1,500 m/sec; and, "f" represents a vibrating frequency of the vibrating elements 10a to 10g (for instance, 500 KHz).

$$\theta = \sin^{-1}\left(\frac{D}{2F}\right) \quad (2)$$

where "$\theta$" indicates an angle of a half sector with respect to the center line.

From the above described equations (1) and (2), the focused region "A" will be defined as follows:

$$A = 2F/(\cot \alpha + \cot \theta) \quad (3)$$

Modification of Geometrical Arrangement

Figure 7:
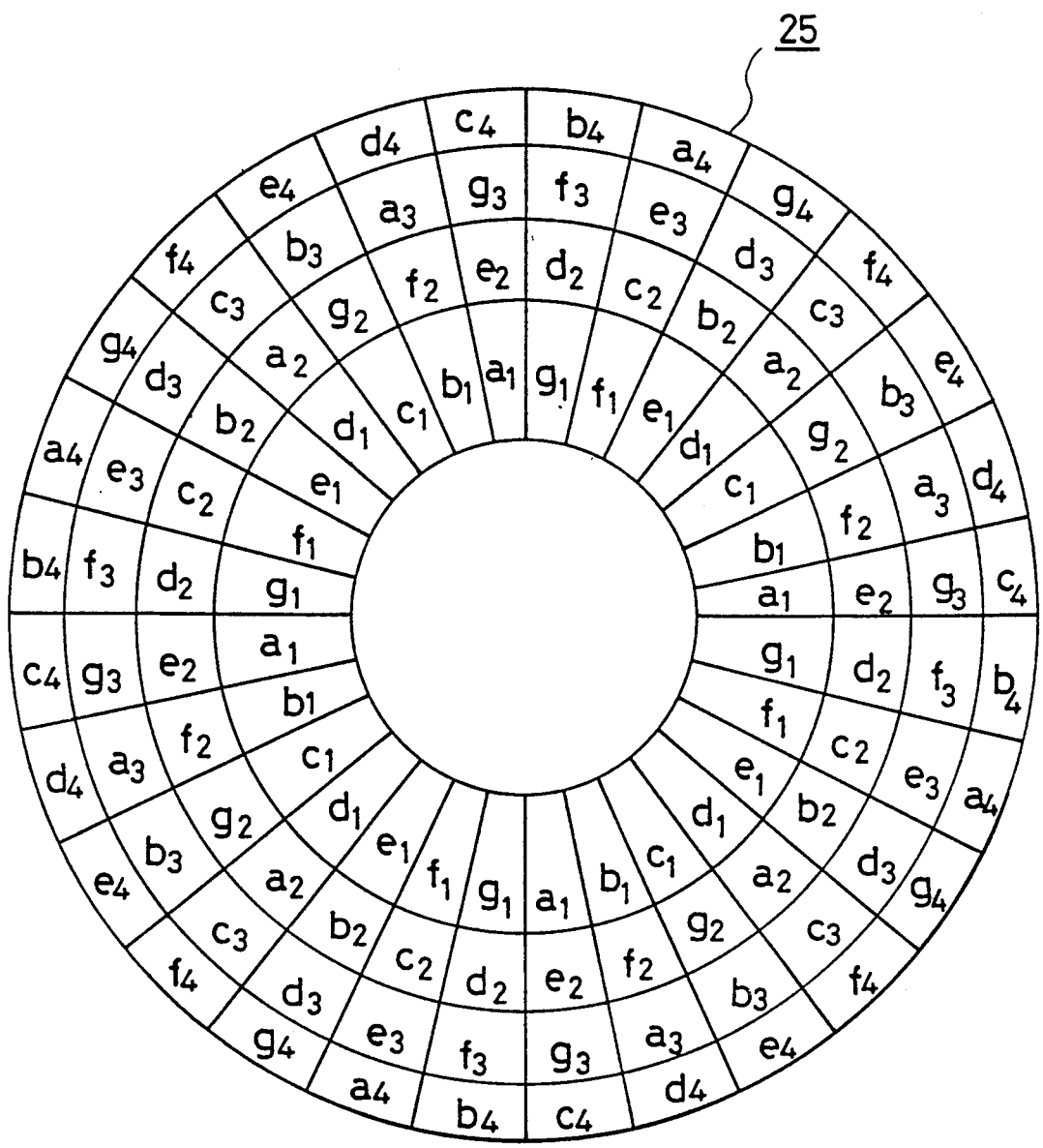
FIG. 7 schematically illustrates a geometrical arrangement of another shock wave applicator 25.

In FIG. 6B, as previously explained, each of the above-described vibrating element groups 10a to 10g is constructed of two vibrating elements. In accordance with the present invention, each of the vibrating element groups may be alternatively constructed of more than two elements. FIG. 7, there is shown another shock wave generating means 25, as an enlarged view, according to another preferred embodiment. As represented in FIG. 7, the respective vibrating element pieces "a" to "g" are discriminated from each other by applying suffixes 1 to 4 thereto. Accordingly, the first focused region 11a is geometrically defined by the vibrating element groups "a1" to "a4". Similarly, the second to seventh focused regions 11b to 11g are geometrically defined by the vibrating element groups "b1" to "b4" through "g1" to "g4", respectively.

Circuit Arrangement of Second Shock Wave Generator

In the previous preferred embodiment, the respective focused regions were simultaneously formed by positioning the corresponding vibrating element groups under a predetermined geometrical parameter. In addition, such a focused region formation may be performed by an electronic means. That is, a shock wave generating apparatus 200 according to the second basic idea of the invention will now be described with reference to FIG. 8, by which the focused region formation is electronically realized.

Figure 8:
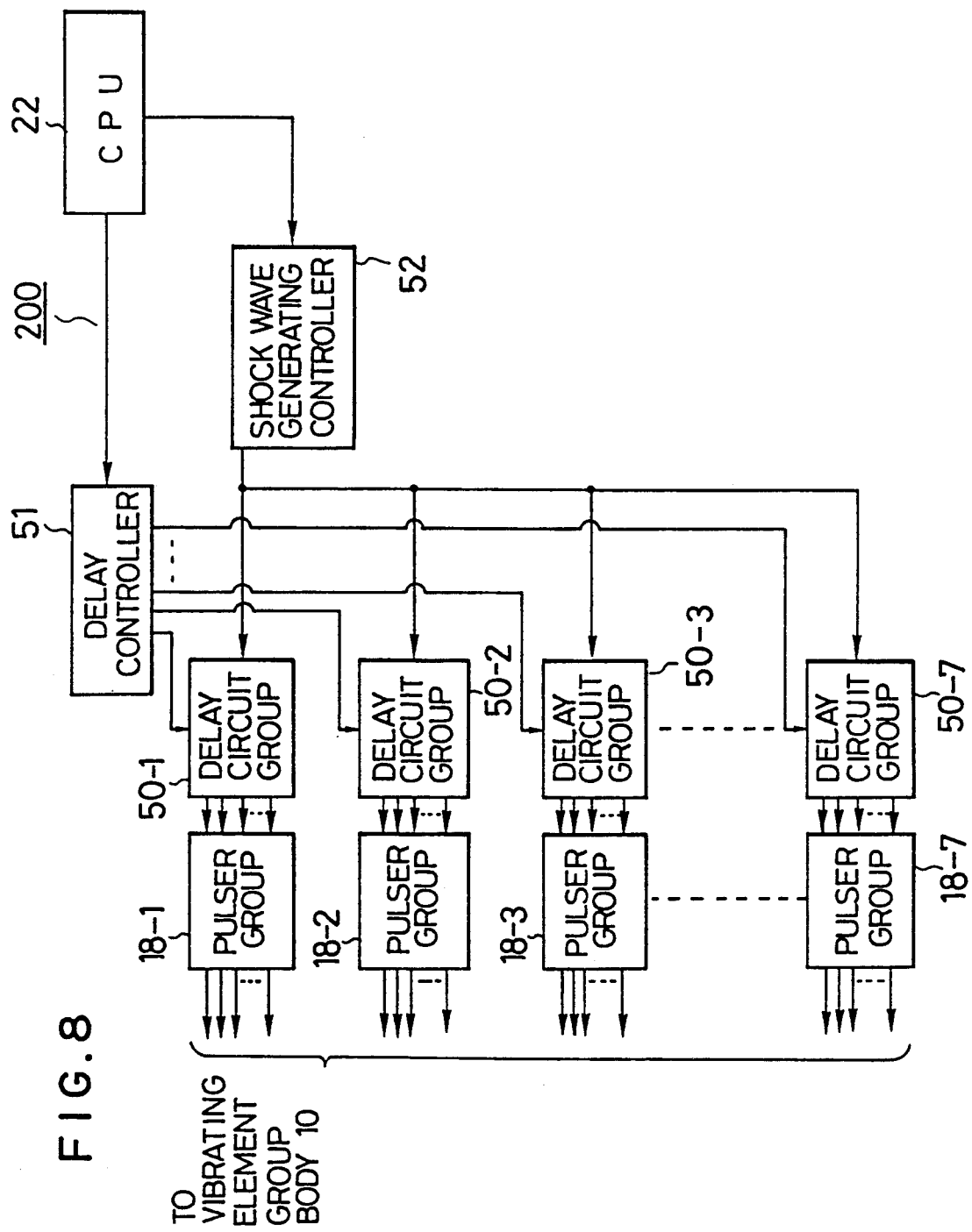
FIG. 8 is a schematic block diagram of a shock wave generating apparatus 200 according to a second preferred embodiment of the invention.

In the circuit diagram of the second shock wave generating apparatus 200 shown in FIG. 8, a plurality of pulser groups 18-1 to 18-n ("n" being a positive integer) are provided, the number of which corresponds to that of the vibrating element groups. In the second preferred embodiment, the number "n" is selected to 7. Each of these pulser groups 18-1 to 18-7 includes a plurality of pulsers, for instance, 4 pulsers (not shown in detail) for the vibrating elements a1 to a4 (see FIG. 7). Delay circuit groups 50-1 to 50-n ("n" being a positive integer, i.e., 7) are connected to the pulser groups 18-1 to 18-n. Similarly, each of these delay circuit groups 50-1 to 50-2 includes a plurality of delay circuits, e.g., 4 delay circuits (not shown in detail). A delay control unit 51 is connected to these delay circuit groups 50-1 to 50-7 in order to control the delay times of the delay circuit groups 50-1 to 50-7. A shock wave generating controller 52 is provided so as to control the generating timings of the shock waves from the vibrating elements. A central processing unit (referred to as a "CPU") 22 is employed to control both the delay controller 51 and shock wave generating controller 52.

It should be noted that although the shock wave generating means is omitted from the circuit diagram of FIG. 8, any types of shock wave generating means may be employed if plural vibrating elements are employed therein, for instance, the shock wave generating means 25 shown in FIG. 7.

Shock Wave Generation By Second Generator

In case that the shock wave generating means 25 represented in FIG. 7 is employed as the shock wave generator for the second shock wave generating apparatus 200, the first pulser group 18-1 is connected to the vibrating elements "a1" to "a4" belonging to the first vibrating element group. Similarly, the second pulser group 18-2 is connected to the vibrating elements "b1" to "b4", and finally the seventh pulser group 18-7 is connected to the vibrating elements "g1" to "g4".

In accordance with the above-described second shock wave generating apparatus 200, the driving timings of the respective vibrating elements, for instance, "a1" to "a4" constituting the corresponding vibrating element groups are controlled by the shock wave generating controller 52 and delay controller 51 in such a way that the plural focused regions formed by the respective vibrating elements connected to the corresponding pulser groups 18-1 through 18-7 are formed at the same time and also juxtaposed each other. Precisely speaking, since the focal distances of the respective vibrating elements are different from each other, depending upon the physical arranging conditions thereof, the driving timings for these vibrating elements are required to be different from each other. That is, based upon the delay times of the delay circuit groups 50-1 to 50-7, which are determined by both the focal distances of the respective vibrating elements and the transfer velocities of the shock waves (typically, 1,500 m/sec), these driving timings of the respective elements are separately determined (see FIG. 6D).

Such a delay control is mainly performed by the delay controller 51. In the second shock wave generating apparatus 200 shown in FIG. 8, the shock wave generation timing signals transferred from the shock wave generating controller 52 are simultaneously fetched by the respective delay circuit groups 50-1 to 50-7. Thus, the driving timings of the respective vibrating elements are adjusted under the control of the delay control unit 51 by applying the preset delay times thereto. As a result, the plural focused regions of the shock waves transmitted from the respective vibrating element groups are simultaneously formed, juxtaposed each other. These focused regions similar to those shown in FIG. 6C can be enlarged, as compared with the conventional focal point 7. In other words, the same or similar advantages of the first shock wave generating apparatus 100 can be also achieved in accordance with the second shock wave generating apparatus 200.

Circuit Arrangement of Third Shock Wave Generator

Figure 9:
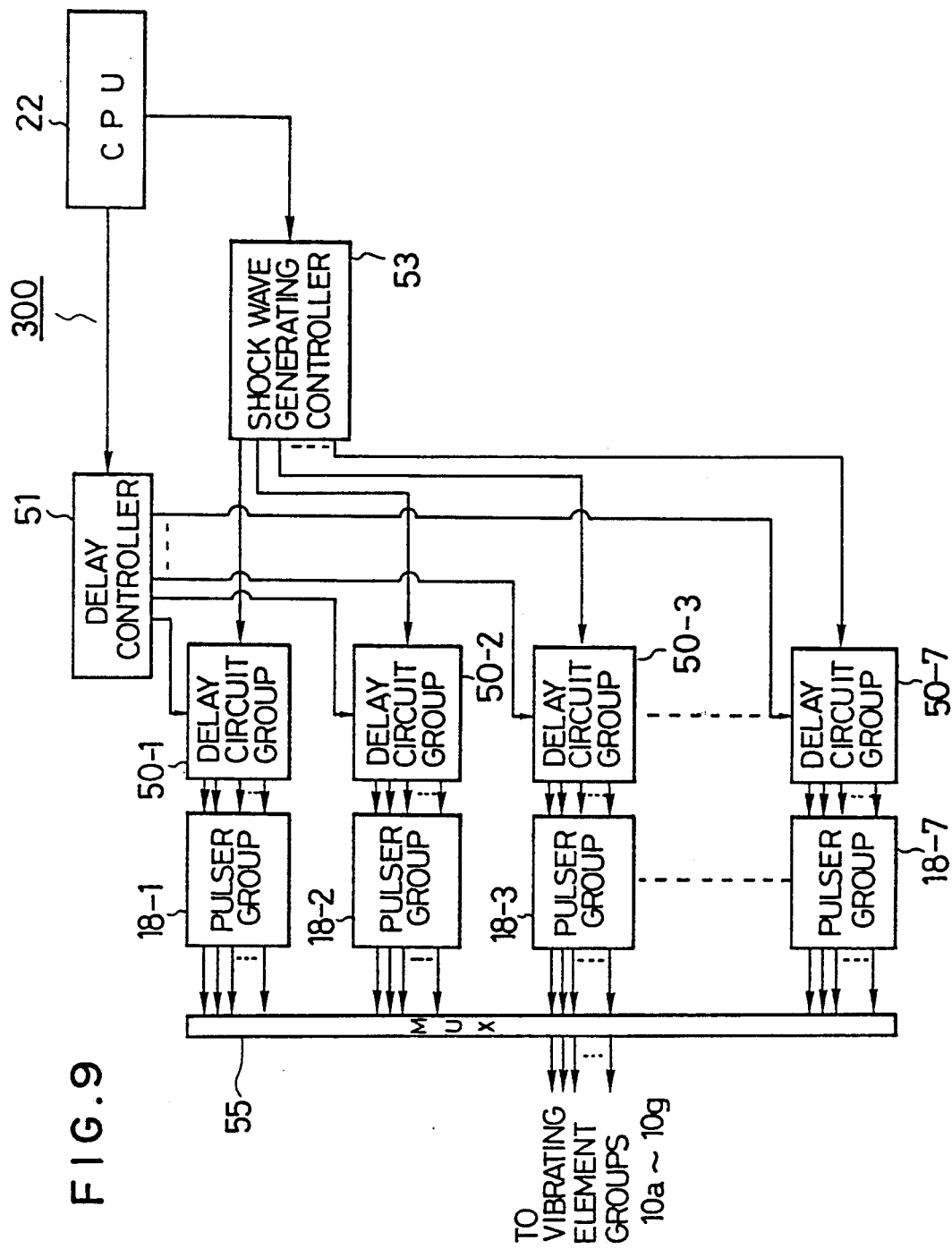
FIG. 9 is a schematic block diagram of a shock wave generating apparatus 300 according to a third preferred embodiment of the invention.
Figure 10:
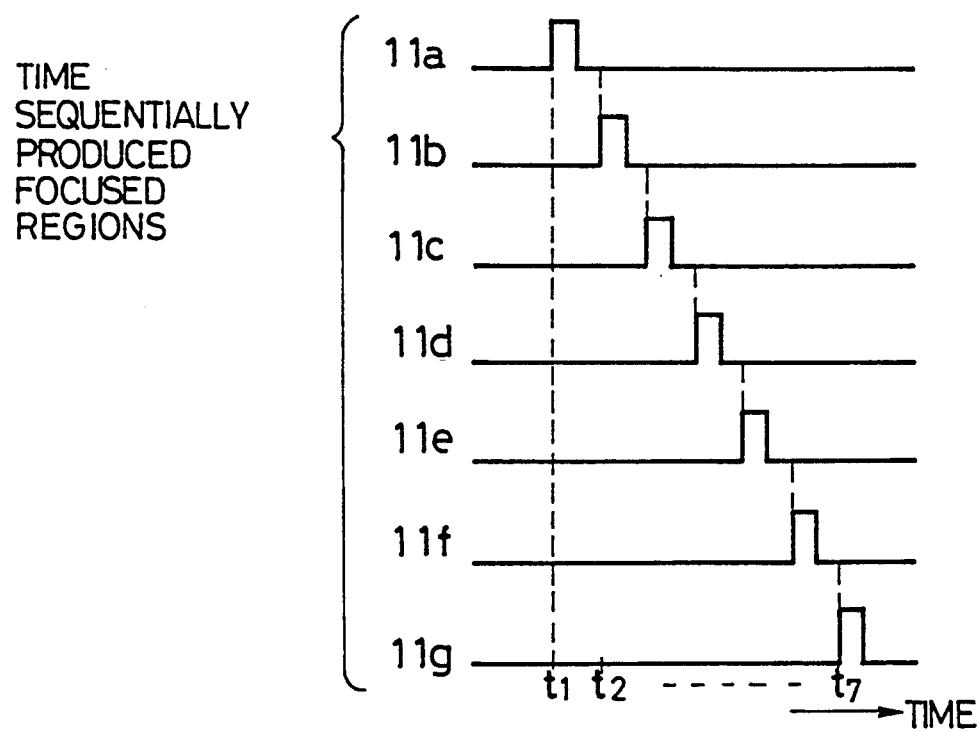
FIG. 10 illustrates plural focused regions sequentially formed by the third shock wave generating apparatus 300; and, FIGS. 11A to 11C are illustrations of a shock wave applicator 80 according to a fourth preferred embodiment of the invention.

Referring now to FIGS. 9 and 10, a shock wave generating apparatus 300 according to a third preferred embodiment will be described, which is accomplished based upon the third basic idea. It should be noted that the same reference numerals shown in FIG. 7 will be employed as those for denoting the same or similar circuit elements in the following figures, and therefore no further explanation is made.

As represented in FIG. 9, the shock wave generating controller 53 is so arranged that the shock wave generation timing signals are separately delivered to the respective delay circuits 50-1 to 50-7. A multiplexer 55 is interposed with the pulser groups 18-1 to 18-7 and the vibrating element groups 10a to 10g. Thus, the high-voltage driving pulses from the respective pulser groups 18-1 to 18-7 are properly selected by the multiplexer 55. One of these pulser groups, for instance, 18-1 is coupled to the first vibrating element group 10a (see FIG. 6B) so that the first vibrating element group 10a is driven by the high-voltage driving pulse, thereby to generate the shock wave therefrom. As a result, the first focused region 11a is formed by the first vibrating element group 10a from a first time instant "t1" to a predetermined time duration (see FIG. 10). Subsequently, the multiplexer 55 is operated so as to couple the next pulser group 18-2 to the second vibrating element group 10b, whereby the second focused region 11b is formed from a second time instant "t2" to a predetermined time duration. Thereafter, the subsequently formed focused regions 11c to 11g will be scanned with respect to the object 8 to be disintegrated.

As previously described, according to the third shock wave generating apparatus 300, the shock wave generation timings can be shifted with respect to the respective vibrating elements under the control of the shock wave generation timing controller 53. In other words, since the shock wave generation timings for the respective vibrating elements are different from each other, the forming timings of the respective focused regions 11a to 11g represented in FIG. 6C can be shifted within a predetermined time duration containing the time instants "t1" to "t7", as illustrated in FIG. 10. As a consequence, the plural focused regions 11a to 11g can be time-sequentially moved over the object 8 to be disintegrated. Thus, the calculus disintegrating efficiency according to the third shock wave generating apparatus 300 may be increased similar to the first and second shock wave generating apparatuses 100 and 200.

Also, in accordance with the third shock wave generating apparatus 300, since the multiplexer 55 is interposed between the pulser groups 18-1 to 18-7 and the vibrating elements 10a to 10g, a total number of the signal lines to the respective vibrating elements 10a to 10g can be considerably reduced, as compared with those of the second shock wave generating apparatus 200. As a result, such a reduction in total number of the signal lines to which the high-voltage driving pulses must be applied, can make a great contribution to an actual product of the shock wave generating apparatus according to the invention.

Lens Focusing Type Shock Wave Applicator

As is apparent from the foregoings, the present invention is not restricted to the above-described preferred embodiments, but may be modified, substituted, and changed without departing from the technical scope of the invention.

Figure 11A:
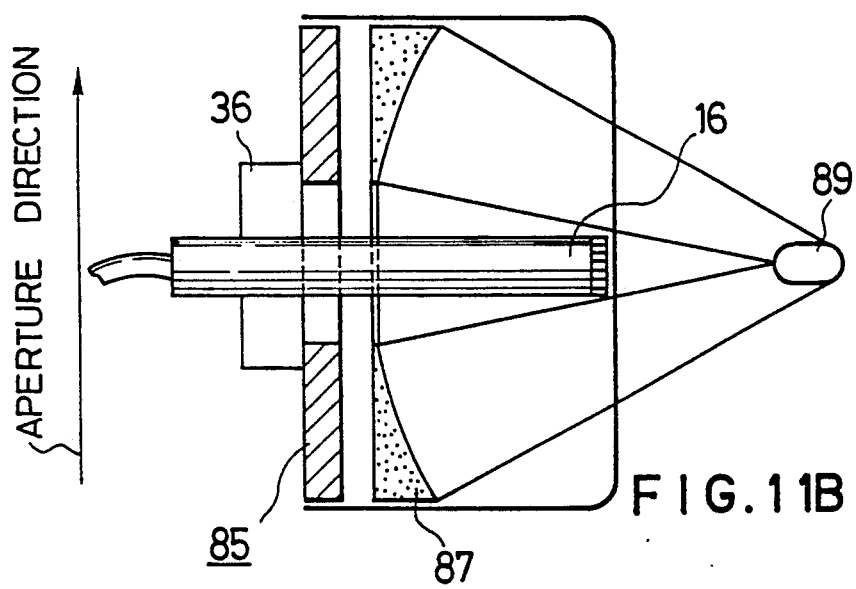
Figure 11B:
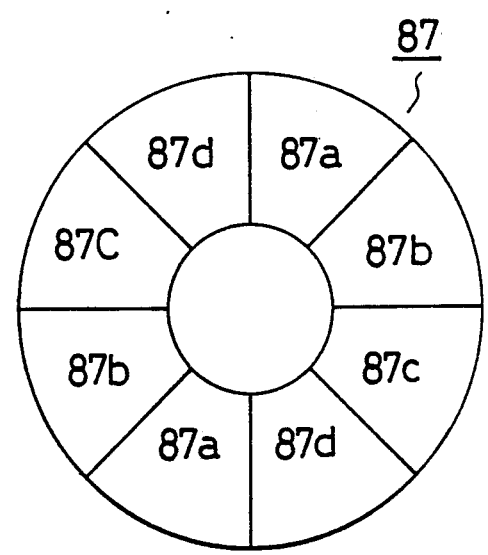
Figure 11C:
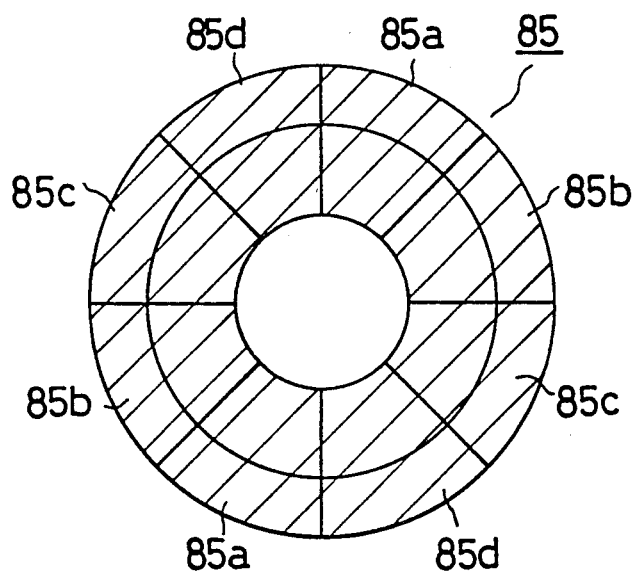

For instance, a lens focusing type shock wave applicator 80 may be constructed based upon the first basic idea, as illustrated in FIG. 11A. Referring now to FIGS. 11A to 11C, this applicator 80 will be described in detail. A major feature of the lens focused type shock wave applicator 80 is to focus shock waves generated from a flat vibrating element group onto a plurality of desirable focused regions by employing an acoustic lens. As obvious from the sectional view of FIG. 11A, the flat vibrating element group 85 for the disintegrating purposes is employed and an imaging probe 16 is inserted into a center portion of this flat vibrating element group 85. An acoustic lens 87 is mounted in front of the flat vibrating element groups 85 in the direction of the shock wave transmission. Thus, the shock waves generated from the flat vibrating element group 85 and focused by this acoustic lens 87 so as to form a desirable focused region 89. This acoustic lens 87 is subdivided into 8 lens portions 87a to 87d as illustrated in FIG. 11B. Precisely speaking, this acoustic lens 87 is divided into 4 pairs of lens portions 87a to 87d. The index of refraction of the respective lens portions 87a to 87d is difference from each other, so that the shock waves which have been generated from the respective vibrating elements and have passed through the acoustic lens 87, are focused onto the different focused regions. That is, according to the effects of the acoustic lens 87, the wide focused region 89 represented in FIG. 11A can be formed from four different focused regions. In FIG. 11C, there is shown a plan view of this vibrating element group 85. As is apparent from this figure, this vibrating element group 85 is subdivided into 4 pairs of vibrating element portions 85a to 85d, similar to the four pairs of lens portions 87a to 87d. Furthermore, one vibrating element portion 85a–85d is subdivided into two small vibrating element sections. As a result of such a small element section, the driving efficiency for these small element sections can be furthermore improved.

Then, the lens focusing type shock wave applicator 80 is coupled to, for instance, a shock wave generator (not shown in detail) similar to the first shock wave generator 100 shown in FIG. 3, and four pairs of vibrating element portions 85a to 85d are simultaneously driven whereby a desirable focused region 89 can be simultaneously formed. Similarly, this lens focused type shock wave applicator 80 may be coupled to another shock wave generator (not shown in detail) similar to the third shock wave generator 300 represented in FIG. 9, and four pairs of vibrating element portions 85a to 85d are successively driven so that small focused regions are successively formed so as to finally form such a wide focused region 89.

While has been described in detail, in accordance with the shock wave generating apparatus of the present invention, the disintegrating efficiency for the object to be disintegrated, e.g., calculus can be increased.

What is claimed is:

1. A shock wave generating apparatus comprising:
   a plurality of high-voltage pulse generating means for generating a plurality of high-voltage pulses;
   shock wave generating means having a plurality of ultrasonic vibrating element groups, coupled to said plurality of high-voltage pulse generating means, for generating shock waves and for focusing the shock waves onto a plurality of different focused regions within a biological body under examination; and,
   a plurality of delay means coupled via said plurality of high-voltage pulse generating means to said plurality of ultrasonic vibrating element groups, for causing said plurality of high-voltage pulses to be generated from the high-voltage pulse generating means with predetermined delay times, whereby the plural focused regions are simultaneously formed juxtaposed each other near an object to be disintegrated within the biological body.

2. A shock wave generating apparatus as claimed in claim 1, wherein each of said ultrasonic vibrating element groups comprises one pair of piezoelectric transducer elements.

3. A shock wave generating apparatus as claimed in claim 2, wherein said piezoelectric transducer elements are arranged in an endless circular form having a spherical shape, as viewed in a section thereof.

4. A shock wave generating apparatus as claimed in claim 1, wherein said ultrasonic vibrating element groups comprise seven pairs of piezoelectric transducer elements.

5. A shock wave generating apparatus as claimed in claim 1, wherein each of said ultrasonic vibrating element groups comprises four piezoelectric transducer elements and said elements groups are arranged in an endless circular form having a spherical shape, as viewed in a section thereof.

6. A shock wave generating apparatus as claimed in claim 1, wherein said ultrasonic vibrating element groups comprise spherical shock wave generating means whose geometrical parameters, including aperture size and focal distance of each of the vibrating elements, define said focused regions.

* * * * *